United States Patent [19]

De Lasa

[11] Patent Number: 5,102,628
[45] Date of Patent: Apr. 7, 1992

[54] RISER SIMULATOR

[75] Inventor: Hugo I. De Lasa, London, Canada

[73] Assignee: The University of Western Ontario, Ontario, Canada

[21] Appl. No.: 196,288

[22] Filed: May 20, 1988

[30] Foreign Application Priority Data

May 21, 1987 [CA] Canada ................................ 537669

[51] Int. Cl.⁵ ...................... B01J 8/20; G01N 31/10; F27B 15/20
[52] U.S. Cl. .................................. 422/140; 422/139; 422/144; 422/227; 422/228; 422/239; 422/269; 436/37
[58] Field of Search ............... 422/139, 140, 144, 227, 422/228, 239, 206, 261, 269, 275; 436/37

[56] References Cited

U.S. PATENT DOCUMENTS

| | | | |
|---|---|---|---|
| 1,646,454 | 10/1927 | Isaachsen | 422/269 X |
| 3,012,962 | 12/1961 | Dygert | 422/143 X |
| 3,288,567 | 11/1966 | Graham | 422/147 X |
| 3,667,914 | 6/1972 | Penquite et al. | 436/37 |
| 4,594,228 | 10/1986 | Lambert, Jr. et al. | 422/228 X |

Primary Examiner—Robert J. Warden
Assistant Examiner—Amalia L. Santiago
Attorney, Agent, or Firm—Shoemaker and Mattare, Ltd.

[57] ABSTRACT

An apparatus for testing performance of a catalyst in a gaseous phase catalytic reaction for a given reactant comprises a reactor receiving a predetermined quantity of fluid reactant discharging the reaction mixture, including reaction products, from the reactor after a predetermined residence time. The reactor comprises a confined reactor volume with an upflow zone and a downflow zone. A device circulates fluids upwardly through the upflow zone and downwardly through the downflow zone where particulate catalysts in the upflow zone are fluidized by the upward flow of the fluid. The circulating device is adapted to circulate the fluid about the reactor volume at a rate which provides at any moment during the residence time for the reactants an essentially uniform concentration of reactants throughout the reactor volume to simulate conditions in a catalytic riser reactor.

9 Claims, 7 Drawing Sheets

RISER SIMULATOR

FIELD OF THE INVENTION

This invention relates to testing apparatus and method for determining the performance of a catalyst in a gaseous phase catalytic reaction or during regeneration.

BACKGROUND OF THE INVENTION

The art of catalytic cracking reactions has evolved considerably over the past fifteen to twenty years. It was common to employ a fluidized bed of catalyst particles in the catalytic cracking of petroleum feed stock to form desired light oils, gasolines, solvents and the like. Although it is possible with existing testing equipment to predict how a particular catalyst will behave with a given feedstock, the advances in the field of catalytic cracking has led to reactor designs which cannot be predicted by existing test units. There is a considerable lack of suitable reaction data for modelling and simulating the more advanced industrial scale riser catalytic cracking reactor which has typical contact times in the range of two to twenty seconds. There is significant uncertainty as to how to predict performance of industrial scale riser reactors. Hence the use of this technology in the petrochemical industry is severely hindered by the limited data and understanding of fast catalytic cracking reactions of different feedstocks in combination with various catalysts. It is this very data that the technical staff of a refinery needs to make crucial decisions about possible changes in operating conditions, modification of existing units, scaling up, processing of different feedstocks depending upon the source of supply, change of the catalysts, adaptation of the process to new conditions of the ever-changing gasoline market and other like considerations.

The same lack of relevant data applies to the regeneration of cracking catalysts under the conditions of riser regenerators. This is also a crucial matter, because the combustion of coke has a significant influence on the overall thermal balance of an industrial scale refinery. The endothermic heat consumed by the cracking reaction is normally supplied by the heat generated by the coke combustion.

Data about the fast regeneration of cracking catalysts is required to develop new cracker-regenerator configurations where both the regenerator and the cracker are transport line reactors. Several technical advantages can be claimed for transport line regenerators—uniform in control in coke levels in the catalyst at the regenerator exit, improved catalyst performance and selectivity and higher zeolite structure stability.

As mentioned, there are a variety of laboratory scale testing units available to determine the activity of selected catalysts and their effect on catalytic cracking of various feedstocks. An example of such a testing unit is disclosed in U.S. Pat. No. 4,419,328. This patent discloses a conventional fluidized bed controlled by a computer. A continuous flow of hydrocarbons is fed to the unit. In this unit, there is only a similarity between the reactant residence time (few seconds) whereas the catalyst time on stream is 300 seconds to 10,000 seconds. This is a major problem for a true modelling of riser reactors. The patent discloses that the fluidized bed of the reactor is fed with a continuous flow of hydrocarbons that produce fluidization. If the flow is stopped, the bed is defluidized without any continued contacting of the catalysts with the introduced hydrocarbons. Moreover even during the continuous operation of the reactor, no uniform residence time can be secured for the hydrocarbon molecules in the fluidized bed. There is significant dissimilarities existing between the time the reactant molecules contact the catalyst and the time the catalyst is exposed to the reacting hydrocarbon environment. As a result, this system could not in any way adequately simulate the conditions of a riser reactor.

Refiners commonly employ a microactivity test unit to establish the activity of catalysts for particular feedstocks. In conventional fluidized bed processes and the like, such units can be very valuable in saving the refiner millions of dollars per year in product value by predicting the effectiveness of the catalyst used in the cracking unit. The microactivity test unit (MAT) is based on the concept of continuously contacting a hydrocarbon feedstock with a catalyst sample of approximately one gram during a 75 to 100 second residence time. The procedure is defined in ASTM (D3907-80). In the MAT test, the catalyst/oil ratio is defined on a cumulative basis which means that the C/O ratio is obtained after a mass of catalyst contacts a hydrocarbon flow for about 75 to 100 seconds. Then in the MAT apparatus, the C/O ratio depends on the catalyst time-on-stream. This results in a significant difference with the conventional riser reactor units, where the catalyst flow and hydrocarbon flow are set for a given operating condition and the catalyst/oil ratio is not a function of a catalyst time-on-stream.

Another significant difference between the MAT and the riser reactor is with respect to contact times. In a conventional riser reactor, the catalyst and the hydrocarbon stay in intimate contact for about two to twenty seconds before being separated in cyclones. In the MAT unit, however, the catalyst reacts with hydrocarbons for about 75 to 100 seconds.

Additional differences can be found between the riser and MAT unit in the way coke is laid down on the catalyst. While in the riser, the coke concentration is only the function of catalyst residence time, in the MAT the coke concentration depends on both the bed axial position and catalyst time-on-stream. Consequently, in the MAT the interpretation of coke deactivation effects and catalytic cracking data is very complex.

This information demonstrates that the MAT technique only allows one to establish relative performance of catalytic materials and is of questionable application or extrapolation to catalytic riser reactors. The kinetic models derived from the data obtained using the MAT are of little use for effectively simulating riser reactors and scaling up thereof.

In accordance with this invention, a testing unit and method is provided which simulates the reaction conditions in a catalytic riser reactor. The system may be used to accurately predict the activity of a catalyst for a given feedstock as well as the conditions of regenerating catalysts.

SUMMARY OF THE INVENTION

According to an aspect of the invention, an apparatus for evaluating processing conditions in the presence of a particulate catalysts comprises a reactor, means for introducing a predetermined quantity of fluid reactant into the reactor and means for withdrawing a reaction mixture including reaction products from the reactor after a predetermined residence time for reactants in the reactor. The reactor comprises a confined reactor volume with an upflow zone and a downflow zone. Means in the reactor volume is provided for continuously circulating fluids in the reactor volume upwardly through the upflow zone and downwardly through the downflow zone. Means for containing in the upflow zone a predetermined quantity of particulate catalysts is provided. The containing means has a screen inlet and screen outlet. The containing means is of sufficient volume to permit fluidization of the particulate catalyst in the containing means by the fluid flowing upwardly therethrough to form a fluidized bed of catalyst particles. The circulating means is adapted to circulate the fluid about the reactor volume at a rate which provides at any moment during the residence time for the reactant an essentially uniform concentration of reactants throughout the reactor volume to simulate thereby conditions in a catalytic riser reactor. The circulating means circulates reactant fluid at the prescribed rate immediately upon the reactant introduction means introducing reacting fluid to the reactor.

According to another aspect of the invention, a method for testing performance of a catalyst for a gaseous phase catalytic reaction conducted in a conventional riser reactor comprises developing a fluidized bed of a predetermined quantity of catalyst particles to be tested in a reactor chamber. The chamber has an upflow zone in which the catalyst particles are fluidized by a flow of inert gases and a downflow zone. The gases are circulated through the upflow and downflow zone. Gaseous reactants are introduced at a predetermined temperature into the reactor and then flow into the reactor is closed off to retain the reactants in the reactor. The catalyst particles are maintained around a predetermined temperature. The reactants react in the presence of the catalyst to produce a reaction mixture including reactant products. The reaction mixture is recirculated rapidly through the downflow zone to provide at any moment during the catalytic reaction an essentially constant reactant concentration in the reactor chamber to simulate catalytic reaction conditions in the conventional riser reactor. The reaction mixture is retained in the reactor chamber for a predetermined residence time. The reaction mixture is withdrawn from the reactor chamber after the predetermined residence time is expired, into an environment which essentially immediately ceases further reaction. The reaction mixture is analyzed for reaction product composition to determine activity of the catalyst at the predetermined temperature for the catalyst bed.

BRIEF DESCRIPTION OF THE DRAWINGS

Preferred embodiments of the invention are shown in the drawings, wherein.

DETAILED DESCRIPTION OF THE PREFERRED EMBODIMENTS

The test unit, according to a preferred aspect of the invention, will be exemplified with respect to testing performance of catalysts in cracking reactions conducted in catalytic riser reactors. Also, the effectiveness in decoking (regenerating) the catalyst will be demonstrated with this test unit. It is appreciated that a variety of catalytic reactions of similar conditions may also be readily tested in this unit while employing the principles of the invention to be exemplified hereinafter.

Figure 1:
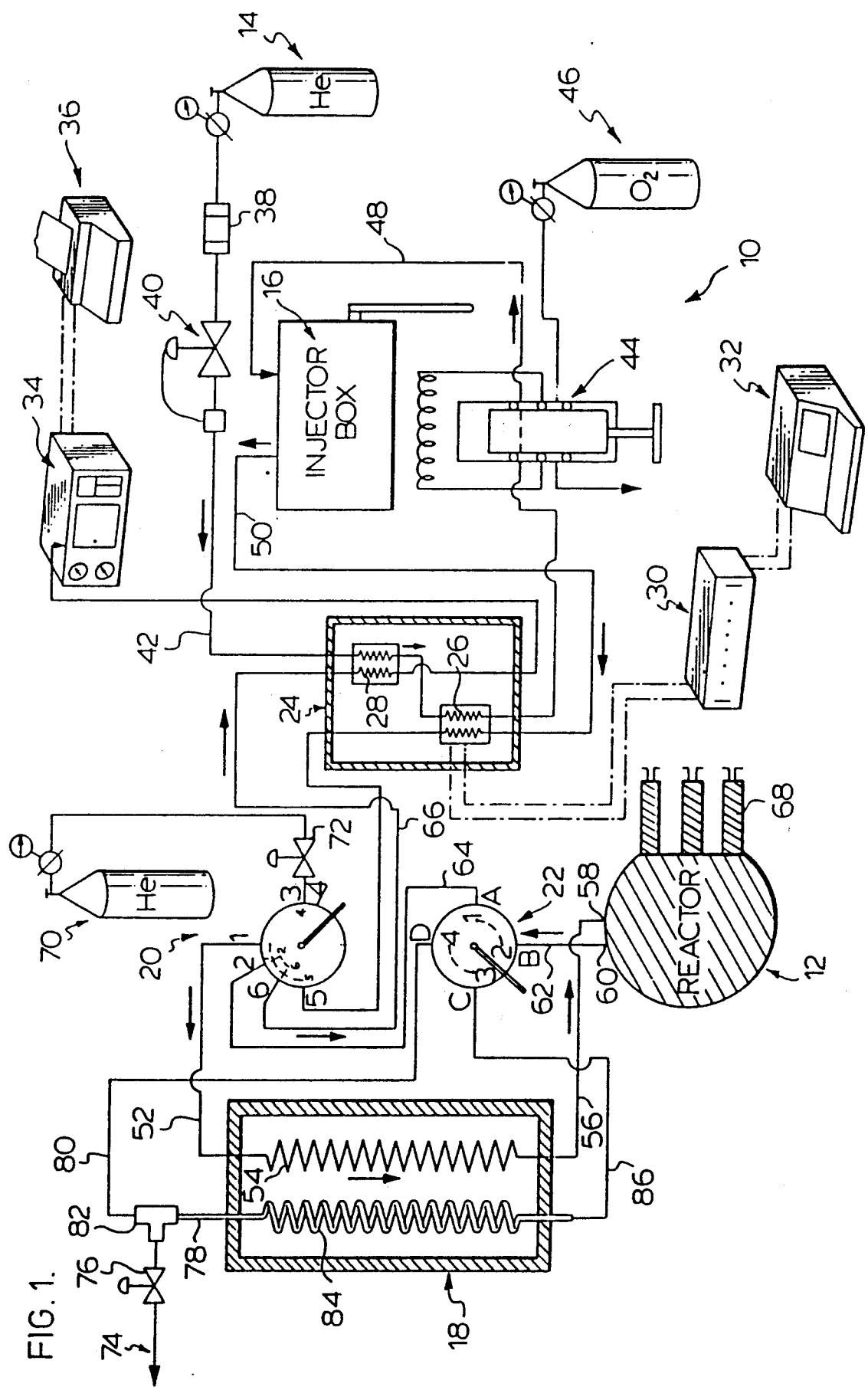
FIG. 1 is a schematic view of the testing unit.

With reference to FIG. 1, a schematic of an exemplary test unit is shown. The test unit generally designated 10 has a reactor 12. A carrier gas in the form of helium is supplied by cylinder 14. When the test unit is used to determine the effectiveness of the predetermined catalyst for a given feedstock, the injector system 16 is used to inject into the carrier gas a predetermined quantity of hydrocarbon feedstock material. A constant temperature enclosure or box 18 is provided which has a preset temperature. The heater box 18 is used to maintain the hydrocarbon sample at a predetermined temperature before introduction to the reactor 12. All flows of fluids through the various conduits are controlled by two valves 20 and 22. Valve 20 controls the admission of fluids to the reactor 12, whereas valve 22 controls the withdrawal of fluids from the reactor 12. Presence of hydrocarbons in incoming and outgoing streams of reactants and reaction products are determined within thermal conductivity measuring system 24 having thermal conductivity measuring devices 26 and 28. The temperatures, as indicated by electrical signals generated in sensors 26 and 28, are fed to an analog to digital converter 30 which in turn has an output to microprocessor 32 for recordal of relevant data. The reaction mixture, as withdrawn from the reactor 12, is fed to a gas chromatograph 34 for analysis of the product composition. The output of the gas chromatograph is then fed to the integrator 36 for printout of the results.

The testing unit is set up to test hydrocarbon feedstock as would be injected by the injector box 16. The temperature of the injector system is set at approximately 150° C. A pump is provided in the injector system to circulate the hydrocarbon feedstock to provide a homogeneous hydrocarbon sample. The thermal conductivity detectors 26 and 28 are brought to a temperature of approximately 350° C. while the temperature of the coil constant temperature enclosure 18 and the valves 20 and 22 are heated to a temperature of approximately 300° C. The temperature of the reactor 12 is set and controlled at the level chosen for the test run. Heating tapes or the like may be used to heat the various conduits of the system while adequate sensors are employed to monitor the temperature in the lines. The temperature selected for the lines may be in the range of 300° C. to 400° C.

The inert helium carrier gas from tank 14 flows through filter 38 and mass flow controller 40. The helium flows through line 42 which passes through the non-sensing side of the thermal conductivity detector 28 and also through the non-sensing side of the thermal conductivity detector 26 before flowing through to the valve 44 for the injector system 16. The valve 44 is also connected to an oxygen supply tank 46 which supplies oxygen in the catalyst regeneration cycle which will be discussed with respect to another embodiment of the invention.

The inert carrier gas continues to flow through line 48 into the injector system 16. The carrier gas exits the injector system via line 50 which passes through the sensing side of thermal conductivity detector 26 and into valve 20 via port 5. For the first position of the valve 20, port 5 is connected to port 1 to deliver the inert gas via line 52 into coil 54 and then through line 56 into the inlet 58 of the reactor 12. The inert carrier gas emerges through outlet 60 of the reactor 12 to valve 22 at port B via line 62. For the first position of valve 22, port B is connected to Port A to deliver the carrier gas via line 64 back to valve 20 at port 2. For the first position of the valve 20, port 2 is connected to port 6 to deliver the gas via line 66 through the sensing side of thermal conductivity detector 28 to the gas chromatograph 34.

Once all temperatures in the test system have reached steady state and the heaters 68 for the reactor are also at steady state, a sample feedstock of hydrocarbon may be injected into the carrier stream. At this point, adequate current for the thermal conductivity detector is selected. At the same time, the other components of the data acquisition system including the Hewlett-Packard 6940 Multiprogrammer and Hewlett-Packard 9826 microprocessor are in the ready condition. A valve, not shown, for the feedstock injection system is switched to the load position in order to introduce into the inert helium gas stream of inlet line 48 a hydrocarbon pulse of approximately 2 microliters. The hydrocarbon pulse is immediately vaporized in the heated injection system and carried by the helium through line 50 towards the sensing side of thermal conductivity detector 26.

Once the pulse size and shape are determined by the thermal conductivity detector 26, the hydrocarbon feedstock sample continues its circulation through line 50 to valve 20, then via port 1 into the coil 54 of the coil heater system 18. At this point in the run, the valve 20 is switched to a second position, such that ports 1 and 3 are connected and ports 2 and 4 are connected. Delay of about five seconds is required between the hydrocarbon injection and the switching of the valve 20 to the second position to trap all hydrocarbon sample in the heater coil 54.

In changing the position of valve 20 to the second position, this modifies the operation of the testing unit from the continuous mode to the discontinuous mode of operation for the reactor. The reactor unit is then isolated from the remainder of the set up. The inert carrier gas continuously circulates through the thermal conductivity detectors 26 and 28 the injector system 16 and the gas chromatograph 34. This is achieved because the valve 20 in its second position provides for interconnection of ports 5 and 6. The inert carrier gas then circulates without interruption, thereby keeping the operation of the thermal conductivity detectors and the gas chromatograph unit under steady state operation, minimizing oscillations or changes in the output signals of these instruments.

With the hydrocarbon sample positioned in coil 54, the sample is ready for injection into the reactor which is heated to a desired temperature in the range of 500° C. to 700° C. To accomplish this, the helium container 70 is connected to port 3 of valve 20 by an additional valve 72. With valve 20 in the second position, port 3 is connected to port 1. Valve 72 is therefore opened and the hydrocarbon sample in coil 54 is immediately fed into the reactor 12. Intense mixing occurs in the fluidized bed of the reactor 12 where all catalyst particles are essentially surrounded by a hydrocarbon mixture of the same composition at any given time. The manner in which this is accomplished will be discussed with respect to the particular views of the reactor structure. A predetermined residence time for the hydrocarbon mixture is provided. When that time is expired, valve 22 is moved to a second position to connect port B with port C and port A with port D. Meanwhile it is noted that valve 72 is shut off after sufficient helium gas has been introduced to inject the hydrocarbon sample from the coil 54 into the reactor.

To establish a rapid withdrawal of the reaction from the reactor, this is accomplished by use of a source of vacuum generally designated 74 which is controlled by valve 76 as connected to line 78 and 80 at T coupling 82. The valve 76 is opened to apply vacuum to the lines and coil 84 and is then shut off. The vacuum coil 84 is at the same temperature as coil 54 in the range of 300° C. to 350° C. depending upon the setting. Also, the coil is at a very low pressure. By now moving the valve 22 to the second position, vacuum as established in the lines is applied to the reactor to immediately withdraw the reaction mixture through outlet 60 and via line 62 through ports B and C through line 86 into coil, 84. Due to the speed at which the reaction mixture is withdrawn from the reactor, further transformation of the products evacuated from the reactor are quickly and effectively stopped. In addition, the controlled temperature in the heater box 18 is sufficiently low in the range of 300° C. to 350° C. to stop further reaction without risking condensing of products in a vacuum coil.

Now that the reaction mixture has been removed and no further reaction can continue, it is necessary to deliver the reaction mixture from the coil 84 to the gas chromatograph 34. The hydrocarbon sample is now located in the coil 84. The coil 84 is then pressurized by helium gas supplied from the helium container 70. With the valve 22 in the second position with port A and D interconnected and with ports 5 and 6 interconnected for the second position of valve 20, the helium gas flows through valve 22 out port D and through line 80 to the T coupling 82. With the vacuum shut off, the pressurized helium pressurizes the coil 84 until the pressure level in the reactor and auxiliary lines becomes very close to the pressure of the thermal conductivity detectors in system 24. Because of the direction of flow, the repressurization provides extra assistance in purging any remaining hydrocarbon product fractions from the reactor 12.

By switching valve 20 back to its first position with port 1 connected to port 5 and port 2 connected to port 6, the continuous flow of inert helium is re-established through the reactor 12. The hydrocarbon product sample, as located in line 62, circulates through the set up via ports B and A as reconnected at position 1 for valve 22, through connected ports 2 and 6 of valve 20 via line 66 through the thermal conductivity detector 28 and into the gas chromatograph 34. The gas chromatograph analysis is conducted using a liquid nitrogen-cryogenic option in order to have the different reaction products in a single chromatogram as specifically adapted to analyzing the results of the cracking process.

As mentioned the test unit may also be used to test regeneration of catalysts by introducing oxygen via the control valve 44 to regenerate catalyst contained in the reactor 12. To accomplish this, instead of using the feedstock injector system 16, the valve 44 is used to inject a predetermined quantity of oxygen into the inert gas carrier line. With the valves 20 and 22 in the first position, the oxygen injecting valve 44 is pushed to the load position and a pulse of oxygen is introduced to line 48. After contacting the catalyst for a preset time, that can range from two to twenty seconds once the oxygen is introduced to the reactor 12 in the same manner as accomplished in introducing the hydrocarbon sample via the coil 54, the products of combustion which are primarily oxygen, carbon monoxide, carbon dioxide and water, are evacuated from the reactor using the same method as described with respect to removal of the hydrocarbon reaction products from the reactor 12. The products of the coke combustion are analyzed in the gas chromatograph 34 using a CARBOWAX (a trademark of Union Carbide for a polyethlene glycol material) packed column. This type of column provides an adequate separation for the combustion products to evaluate the effectiveness of the regeneration process in regenerating the catalyst.

The testing apparatus 10 provides a continuous flow of inert carrier gas through the system to provide for a steady state condition and then to inject a sample of reactant into the reactor via the carrier gas. At that instance, flow of the carrier gas is interrupted to provide for discontinuous operation of the system. While the reactants are in the reactor, the system is monitored to provide for a predetermined residence time at which point the reaction mixture is rapidly withdrawn from the reactor. As noted, one purpose of the system is to simulate reaction conditions in a conventional catalytic riser reactor. Another object of the system is to simulate the conditions in regeneration of spent catalyst. To accomplish these aspects, the reactor 12 is specially designed to provide at any instance during the residence time of the reactants in the reactor an essentially constant concentration of reactants in any portion of the reactor volume.

Figure 2:
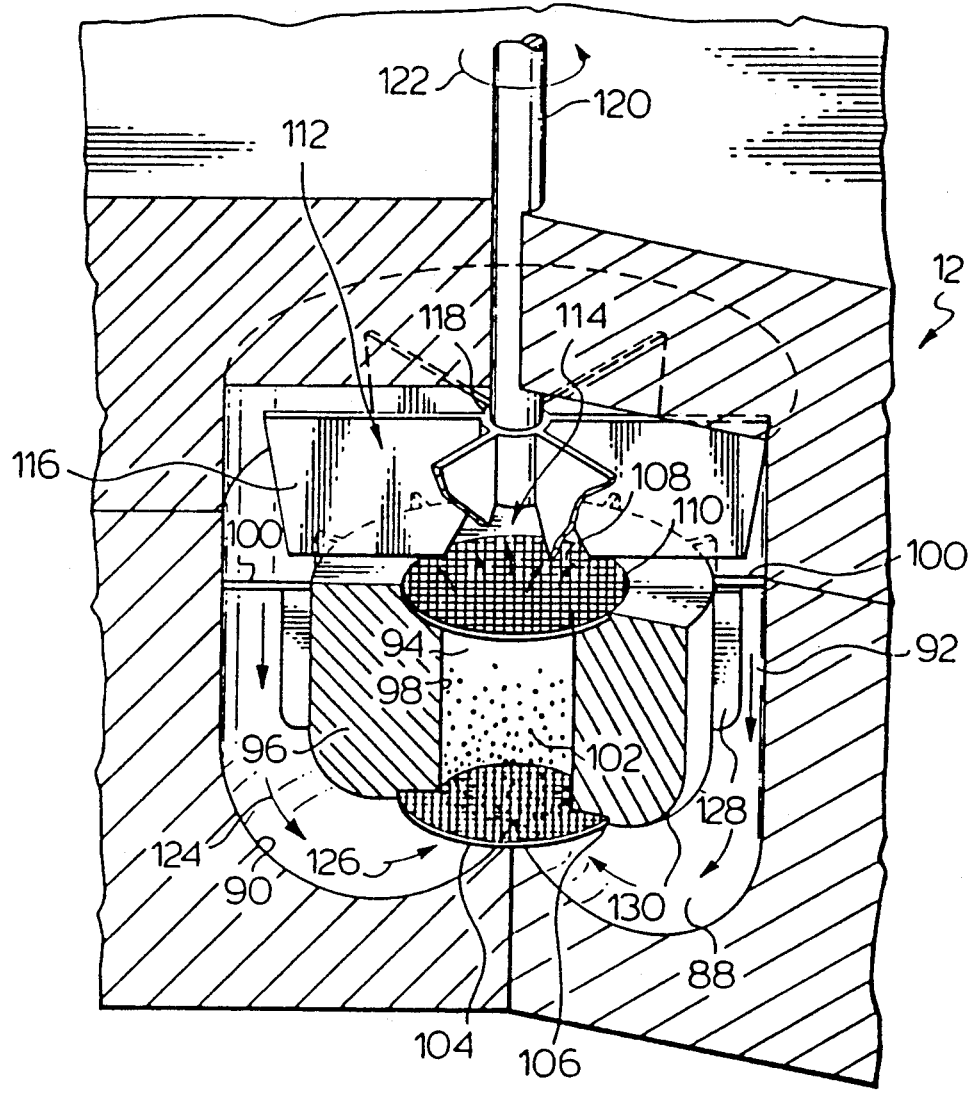
FIG. 2 is a perspective view of the reactor of the test unit of FIG. 1.

With reference to FIG. 2, the reactor 12 has a reactor chamber 88 defined by cylindrical interior surface 90. The reactor chamber 80 consists of an annular downflow zone 92 and an upflow zone 94. These zones are defined by positioning a cylindrical annulus in the reactor chamber 88. The cylindrical annulus 96 has a central core 98 extending vertically therethrough with the reactor in the vertical orientation. The annulus 96 is supported by radially extending cross-members 100. The annulus 96 is formed of a high grade stainless steel, or other suitable metal which is not reactive with the environment. The annulus is of considerable thickness to provide a heat sink which maintains a constant temperature for the fluidized bed of catalyst 102 within the core. The bed of catalyst 102 is maintained in the upflow zone 94 by a first screen 104 at the bottom opening 106 of the baffle. A second screen 108 is positioned at the upper opening 110 of the baffle. Either or both of these screens may be removable to permit replacement of the catalyst 104.

To provide for the desired direction of circulation of inert gases and introduced fluid reactants within the reactor chamber 88, a circulating device in the form of a rotating impeller 112 is employed. The intake region 114 of the impeller 112 is located directly above the outlet screen 108 of the upflow zone. The impeller 112 is provided with a plurality of vanes 116 as readily attached to a hub 118 of the drive shaft 120 for the impeller. The impeller is rotated at very high rpms in the range of 3000 and above by driving the shaft 120 in the direction of arrow 122. For example, the shaft speeds may range as high as 15,000 to 20,000 rpm. This causes a vigorous flow of the fluids in the reaction chamber 88 by moving outwardly from the vanes 116 and downwardly in the direction of arrows 124 and then upwardly through the upflow zone in the direction of arrow 126. The impeller is thus rotated at a sufficient speed to cause the fluids as they flow through the upflow zone to fluidize the bed of catalysts 102 in the upflow zone 94. The volume defined between the inlet and outlet screens 104 and 108 is such to permit fluidization of the bed of catalyst without over compression of same.

Due to the speed at which the impeller 112 rotates, there is a tendency for a vortex to form in the annular downflow zone 92. This is prevented by placing a plurality of radially extending baffles 128 about the outer cylindrical surface 130 of the annular baffle 96. This encourages a downwardly directed flow for the recirculating reaction mixture. The volume of the reactor is such that, by way of the vigorous, rapid recirculation of the reaction mixture in the downflow zone and back into the upflow zone, there is minimal time span between the time when the reaction mixture leaves the outlet screen 108 until it returns to the inlet screen 104. This provides that at any moment during the residence time of the reactants in the reactor, the concentration of the reactants is essentially constant throughout the volume of the reaction chamber 88. This aspect simulates the conditions of a conventional catalytic riser reactor. In that system, there is a contact time in the range of two to twenty seconds where the reactants and the catalyst flow together upwardly through the riser tube. At the top of the tube, the catalyst is extracted from the reaction mixture by way of cyclone devices in accordance with well known standard techniques. With the reactor system of FIG. 2, essentially the same conditions are achieved by providing this well mixed minifluidized bed.

Figure 3:
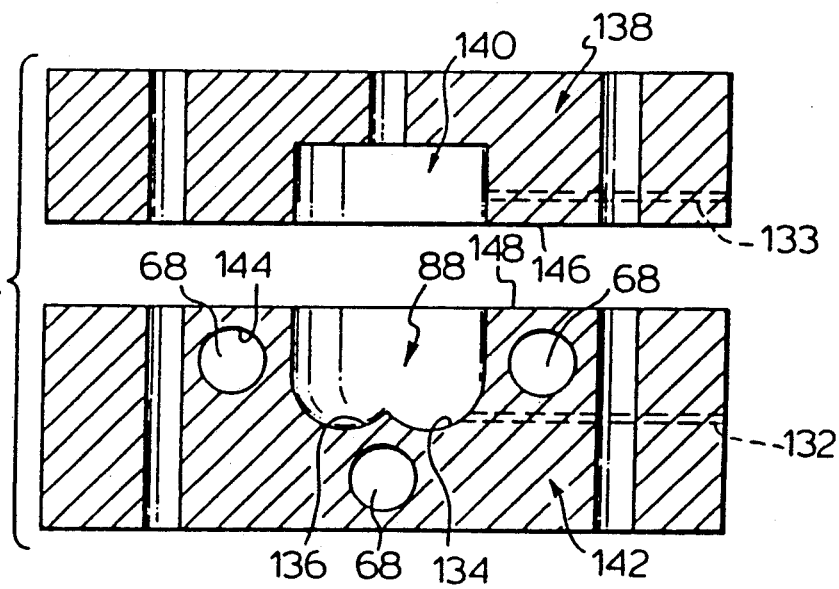
FIG. 3 is an exploded section through the reactor of FIG. 2.
Figure 4:
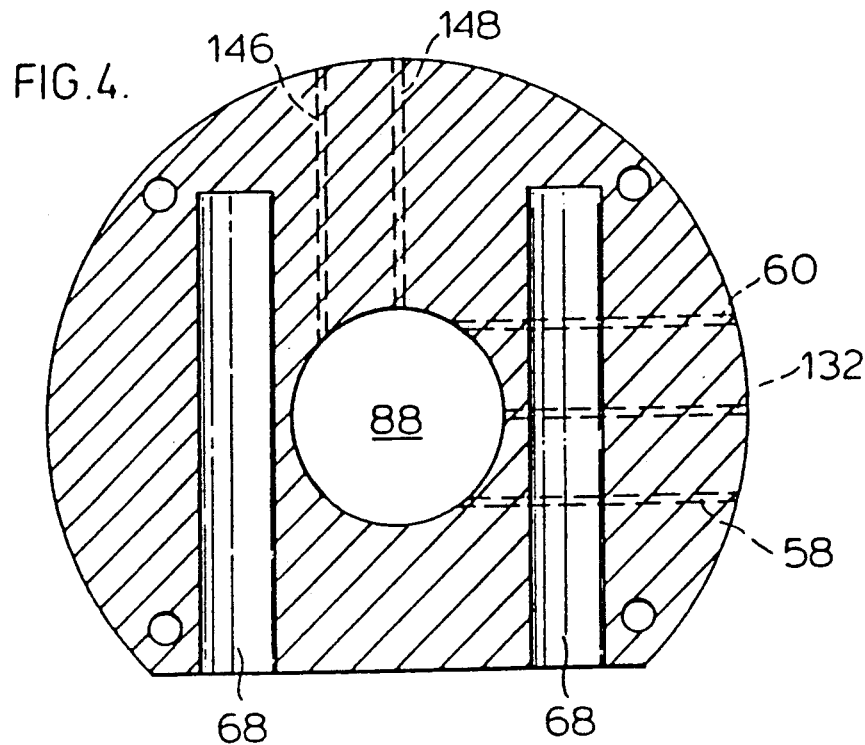
FIG. 4 is a top view of a section of the reactor of FIG. 2.
Figure 5:
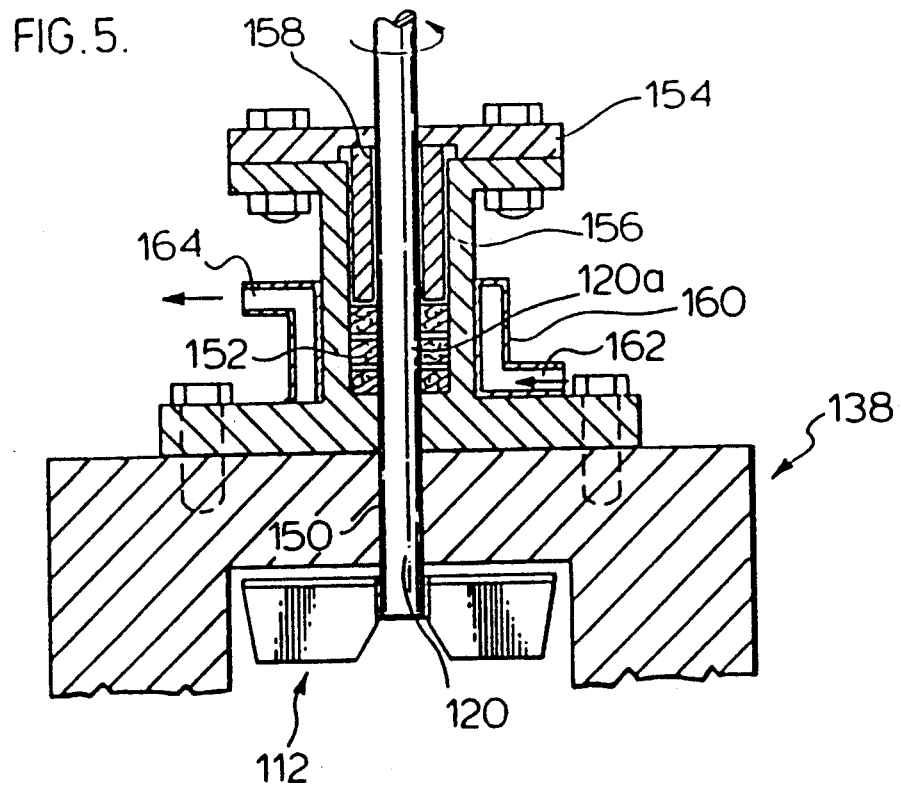
FIG. 5 is a section through the sealing jacket for the impeller shaft.

By locating the impeller 112 at the outlet of the upflow zone, there is little if any tendency for the high speed rotation of the impellers to cause inconsistencies in the miniaturized bed. Hence a more uniform flow of the fluids through the fluidized bed of catalyst is assured. To monitor the quality of the fluidized bed in the upflow zone, two pressure taps are employed as shown in FIGS. 3 and 4. Minute bores 132 and 133 extend into the lower region 134 and into the upper region 140 of the reactor chamber 88. By monitoring the pressure at these points in the reactor, it is possible to determine the consistency of a fluidized bed throughout the run of the testing device. The lower portion 134 of the reactor chamber 88 has a radiused portion at 136 to direct the upward flow of the reaction mixture in the direction of arrows 126 as shown in FIG. 2.

The inlet 58 for the reactor is shown in FIG. 4 which extends through the upper block portion 138 of the reactor into the upper portion 140 of the reactor chamber. The outlet 60 for the reactor also extends through the upper block 138 and communicates with the upper portion 140 of the reactor chamber 88. Hence the reactants are introduced and extracted at the tip portions of the impeller blade 116.

The lower block portion 142 of the reactor carries the heater units 68 in the bores 144. An appropriate controller is provided to heat the reactor to the desired temperature and maintain it at that temperature. In providing such control, thermocouples are located in bores 132 and 133 to monitor the temperature at all times in the system. When it is desired, the reactor is assembled by clamping the blocks 138 and 142 together by use of suitable mechanical fasteners, clamps or the like. The interfaces 146 and 148 are properly machined so as to provide a suitable seal for the reactor chamber 88.

It is important to provide a suitable seal at the interface of the impeller shaft 120 and the body of the upper block 138. The shaft 120 extends through bore 150 and is sealed in the region of 120a by a packing 152. The packing is compressed by way of cap 154 bolted to the packing retainer 156. A sleeve 158 compresses the packing 152 by bolting the flange 154 in place. Due to the high temperatures of the reactor, cooling about the packing retaining body is required to prevent heat from the reactor degrading the packing. A cooling jacket 160 is provided through which cooling water is circulated by inlet 162 and outlet 164. In addition, the cooling ensures that the packing does not overheat during high speed rotations of the shaft 120. In this manner, the reactor chamber 88 is sealed in the region of the impeller as it extends through the reactor block 138.

With this design for the reactor, the conditions of a conventional catalytic riser reactor can be simulated. By suitable operation of the valves 20 and 22 in the manner previously discussed which may be either manually or computer controlled, the switching from continuous flows through the reactor to a discontinuous residence time of reactants in the reactor is readily achieved. This set up therefore allows the monitoring of the amount of hydrocarbon feedstock injected, the quality of the mixing in the reactor vessel, the adequacy of the hydrocarbon injection and the effectiveness of the product evacuation from the reactor by the vacuum withdrawal system.

As is appreciated in the design of the test unit and use of auxiliary components, it is desirable to minimize the dead spaces between the exit of the reactor and the thermal conductivity detectors in order to prevent the distortion of the injected reactant pulse as well as of the eluded products extracted from the reactor. The vaporization system in the injection system is adapted to provide a very rapid vaporization of the hydrocarbon sample prior to injection. The data acquisition system in the microprocessor and gas chromatograph has the appropriate rate of data sampling to monitor the hydrocarbon concentration transients going and returning from the reactor.

For purposes of testing the hydrocracking of hydrocarbons, the reactor is normally operated at a temperature in the range of 500° to 750° C. Hence the reactor must be built of a non-reactive or inert metal which can withstand these temperatures without distorting. A preferred composition of construction is a nickel based material sold under the trademark INCONEL which is available from Inco of Canada. A preferred dimension for the reactor is an overall diameter of six inches with the height being approximately three inches. The diameter of the basket cavity for the fluidized bed of catalytic particles is approximately 1.75 inches. The height of the basket cavity is approximately 1.7 inches. The diameter of the reactor chamber 88 is approximately 1 inch.

Because of the rapid circulation of the reaction mixtures through the reactor chamber, it is possible to use a catalyst to oil ratio which corresponds with the standard catalyst to oil ratio used in conventional catalytic riser reactors. In such conventional systems, the catalyst to oil ratio is based on the flow of catalyst to the flow of oil. Knowing what ratio is used commercially, it is possible to use a corresponding ratio in the reactor system by way of a ratio of the weight of catalyst to the weight of liquid hydrocarbon introduced to the reactor system. Hence correspondency in simulating reactor conditions in the test unit are readily achieved.

As noted, the system is equally applicable to the regeneration of catalysts. In conducting such tests, the reactor is normally run at a temperature in the range of 650° C, to 700° C. to provide for oxidation of the coke on the catalyst surface by the injected predetermined quantity of oxygen into the inert carrier gas.

The reaction mixture, as fed to the gas chromatograph/mass spectrometer with capillary capabilities, is then analyzed to determine the quantity and identity of the reaction products and from this information, the overall effectiveness of the catalyst for the particular reaction conditions in terms of temperatures, C/O ratio and the like is determined. The residence time of the reactants in the reactor is the same as in the conventional riser reactor system, i.e. in the range of two to twenty seconds. Hence this test system provides a very quick evaluation of feedstocks, catalysts and other factors which should be determined in optimizing the overall operation of an industrial scale riser reactor system.

A difference, which the system of this invention which distinguishes over other systems, is that the reactor with internal recycle has an upward flow through the catalyst chamber and with intense internal recycle, there is simultaneously achieved a small fluidized bed of cracking catalyst. Gas flow in this direction is established by locating the appropriate blower above the catalyst bed insert. Suction is created across the bed and the gas flow is directed down the draft tube annulus. The subsequent fluidization of solids prevents coke profiles to be formed during cracking reactions. By trapping a pulse injection of hydrocarbon feed in the reactor and allowing reaction to occur under batch conditions, the transformations which occur when catalyst and oil come into contact in a riser are effectively simulated. Considering the total gas volume in the reactor and the catalyst volume, then an equivalent hold-up of solids, as in a riser may be defined. These catalyst particles see a changing hydrocarbon environment with time in the same manner flowing solids in a riser contact a hydrocarbon mixture of changing composition, while circulating through the transport line.

EXAMPLE 1

An experiment was conducted using the equipment of FIGS. 1 and 2. A draft tube insert containing the central catalyst basket is held in place by a ring support. Catalyst is held in the central tube by 2-20 $\mu$m porous plates (screens). The centrifugal blower, which is a six-blade impeller, is located at the top of the tube insert. Total internal gas volume is 30 ml and total catalyst chamber volume is 2 ml (13.5 mm diameter by 15 mm height). Cartridge heaters located in the Inconel 600 reactor block provide the necessary heat for securing close to constant temperature in the reactor vessel. A motor-pulley system is used to drive the blower and the shaft seal is kept cool by means of a water cooling jacket.

Reactor temperature is monitored by 1/16" diameter thermocouples, one in the catalyst bed which controls the heaters and one in the annulus region. Pressure taps strategically located in the catalyst chamber allow measurement of bed and grid pressure drops.

The operating procedure for the system involves injection of gas oil to the reactor followed by the reaction period, then purging of the reactor products into the valve box and finally sampling of gaseous products to the GC. Initially before injection of gas oil to the reactor, a steady flow of nitrogen was allowed to pass through the reactor to purge and pressurize the reactor.

The impeller was rotated at 9000 rpm and an injection of gas oil was made into the hot reactor. After the specified reaction time period the reactor is evacuated. As soon as the reactor pressure range gauge reached zero, the valve was repositioned to separate any products left in the reactor, which could undergo further cracking past the designated reaction time, from those in the purge lines.

To avoid flooding of the gas chromatograph (GC) capillary column, the total products from the reactor were not sampled at one time. The sample loop was used to send small amounts of the gaseous products to the GC.

After the sampling period, the catalyst was regenerated by connecting a flow of 20% oxygen and 80% helium to the reactor and allowing it to pass continuously through the reactor heated at 650° C. The regeneration period lasted ten minutes to provide near to complete combustion of coke. The reactor was then allowed to cool to the cracking temperature under a steady flow of nitrogen and the injection procedure repeated.

To test the performance of the riser simulator, a commercial paraffinic gas oil was cracked over Octacat catalyst. The catalyst was steamed at 766° C. for 18 hours to produce an equilibrium catalyst which resulted in a 37% reduction in surface area from the fresh catalyst value of 230 m²/g.

The cracking runs involved twelve experimental conditions combining three different catalyst/oil ratios (3, 5 and 7), two reaction times (5 and 10 seconds) and two temperature levels (500° C. and 550° C.) as summarized in Table 1.

TABLE 1

| LIST OF THE 12 EXPERIMENTAL CONDITIONS USED | | | |
|---|---|---|---|
| Experimental Condition | Temperature (°C.) | c/o Ratio | Reaction Time(s) |
| 1 | 500 | 7 | 5 |
| 2 | 500 | 7 | 10 |
| 3 | 500 | 5 | 5 |
| 4 | 500 | 5 | 10 |
| 5 | 500 | 3 | 5 |
| 6 | 500 | 3 | 10 |
| 7 | 550 | 7 | 5 |
| 8 | 550 | 7 | 10 |
| 9 | 550 | 5 | 5 |
| 10 | 550 | 5 | 10 |
| 11 | 550 | 3 | 5 |
| 12 | 550 | 3 | 10 |

At each condition, three repeat injections of gas oil were made, the products from each injection being sampled three times to the GC for analysis. The GC integrator report gave weight distributions of the components and the gas oil yield was calculated by summing components in the range of $C_{13}$ and greater. The gasoline range was based on a $C_5$ to $C_{12}$ cut and the light gases were classified as $C_4$ and smaller. The yields of these three lumps were averaged for the total samples analyzed at each experimental condition.

Figure 6:
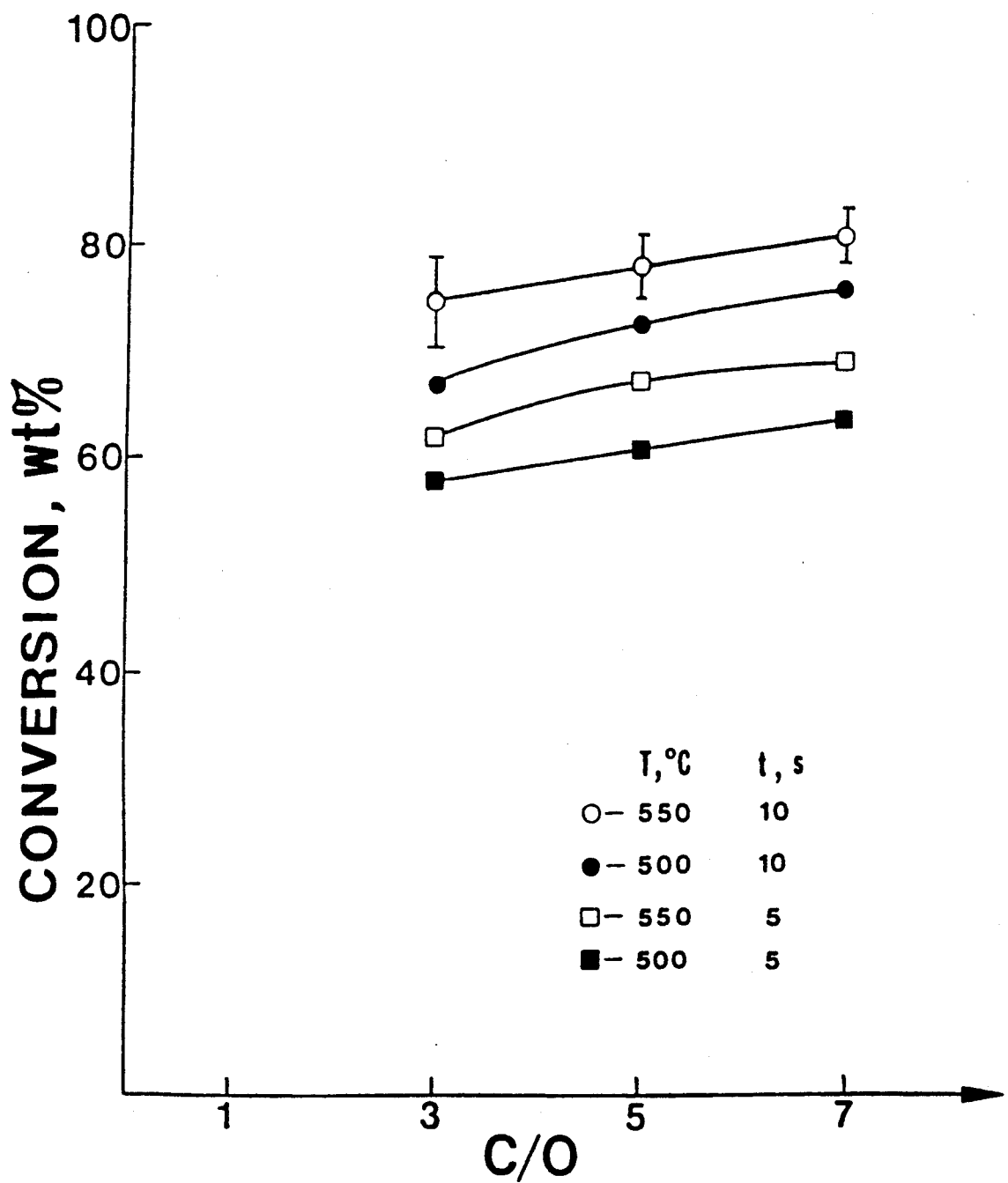
FIG. 6 is a plot of conversion of gas oil versus catalyst to oil (C/O) ratio (error bars are similar to the ones shown for all curves)

The conversion of gas oil against catalyst/oil ratio is shown in FIG. 6 for the two temperatures levels and two reaction times used. The following expected trends were observed:
- at a constant reaction time and temperature, conversion decreased with decreasing C/O ratio;
- at a constant catalyst to oil ratio and temperature, conversion increased with reaction time;
- at a constant catalyst to oil ratio and reaction time, the conversion also increased with temperature.

Figure 7:
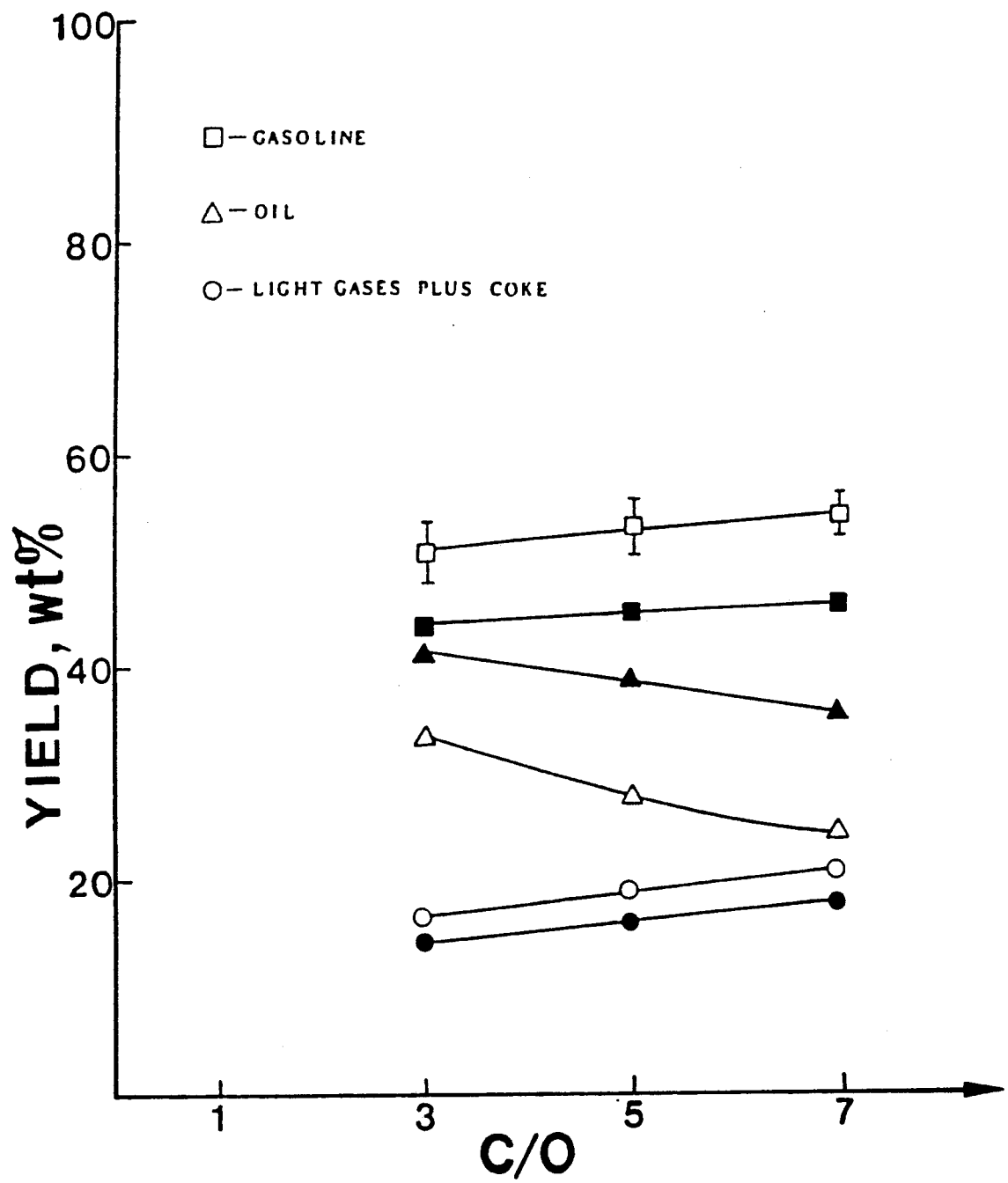
FIG. 7 is a plot of yields of gasoline, light gases plus coke and unconverted gas oil at 500 C versus C/O ratio (darkened symbols refer to 5 seconds reaction time, open symbols for 10 seconds)
Figure 8:
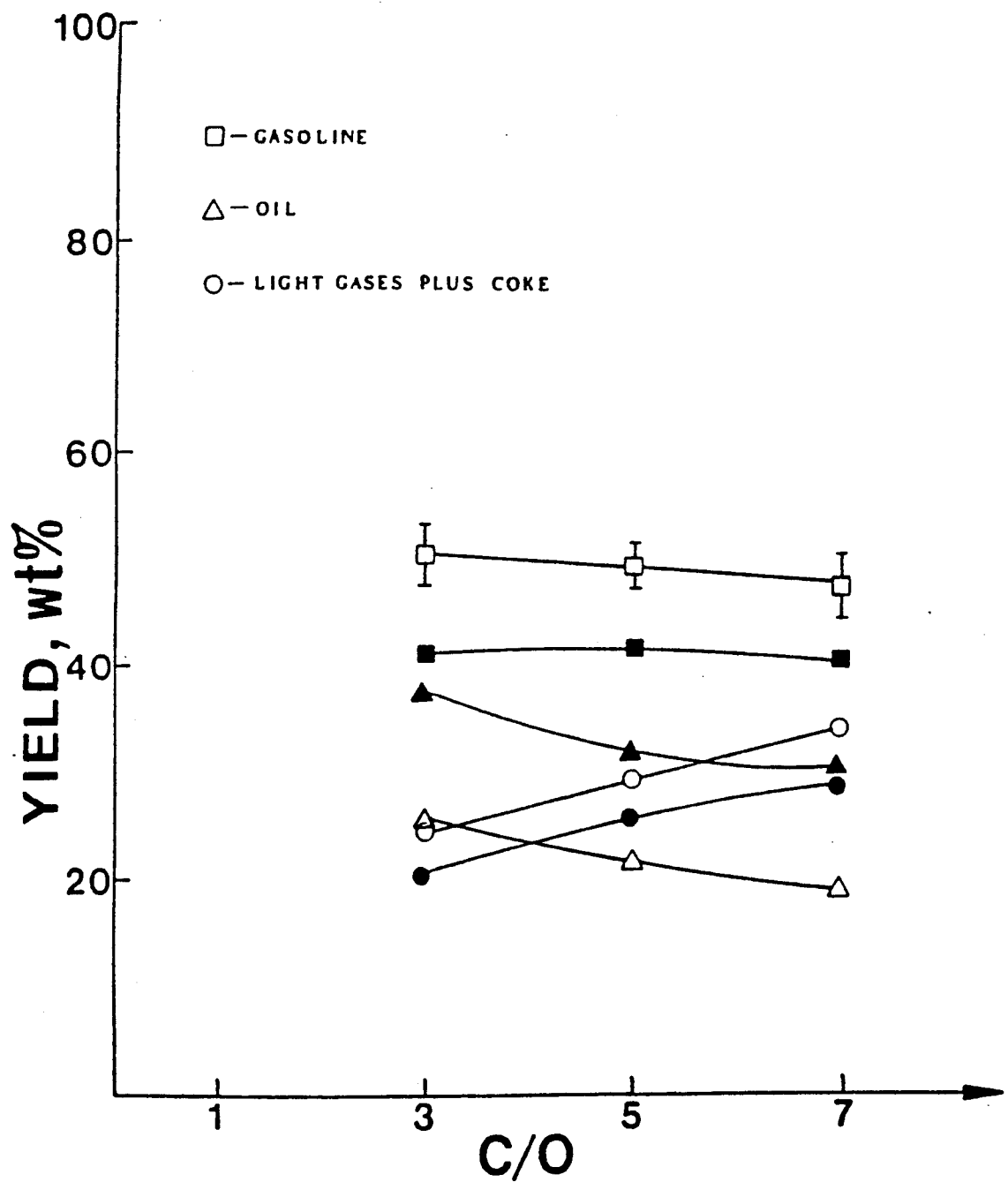
FIG. 8 is a plot of yields of gasoline, light gases plus coke and unconverted gas oil at 550 C versus C/O ratio (darkened symbols refer to 5 seconds reaction time, open symbols for 10 seconds)
Figure 9:
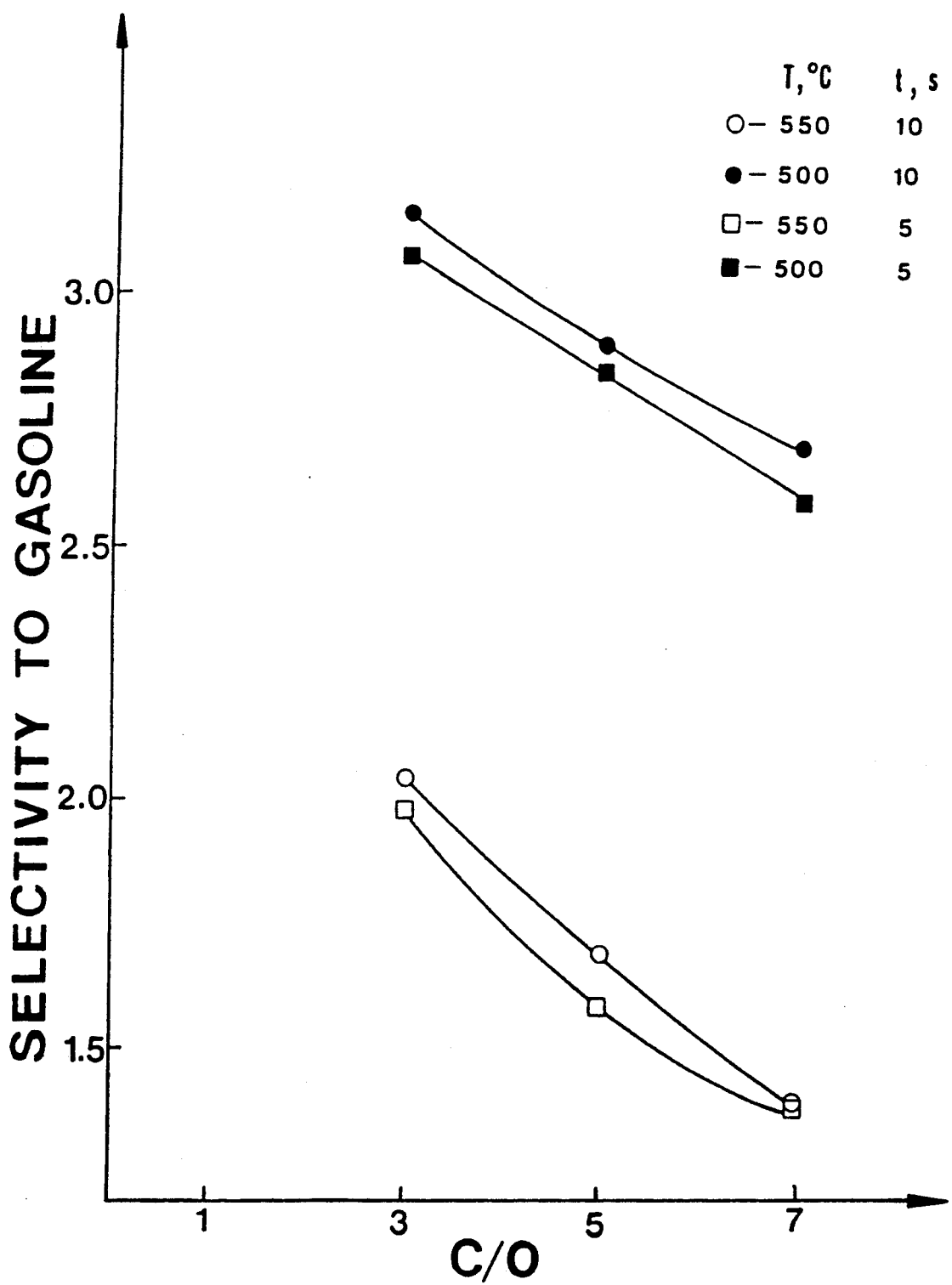
FIG. 9 is a plot of selective to gasoline versus C/O ratio.

To visualize the effects of the operating variables (reaction time, catalyst to oil ratio and temperature) on the lumped product yields, three plots were made (FIGS. 7, 8 and 9). As expected, the yield of gasoline increased with reaction time for the two times considered, at constant catalyst to oil ratio and temperature. FIG. 7 shows that holding reaction time and temperature constant, the yield of gasoline increased slightly with catalyst to oil ratio for both reaction times.

At the higher temperature (550° C.), the gasoline yields were only slightly affected by variations in C/O levels for the two reaction times considered as indicated by FIG. 8.

A more apparent effect on gasoline yield is that of temperature. Comparing FIGS. 7 and 8, it can be observed that for both reaction times, the gasoline yields at 550° C. were lower than at 500° C., for constant C/O levels. The largest decrease was seen at the highest catalyst to oil ratio. This effect of temperature on gasoline yield shows that for the catalyst tested, the same type of trade-off normally involved in catalytic cracking, between increased oil conversion and decreased gasoline yield at higher temperatures, was an important factor.

FIG. 7 also compares the light gases plus coke yields with catalyst to oil ratio at 5 to 10 seconds reaction time and a temperature of 500° C. It is seen that as the C/O parameter increases so does the yield in light gases and coke. The yields are larger at the higher reaction time. Also, the slope of the yield versus catalyst to oil ratio curve is larger for the light gases plus coke product lump than for the gasoline product. This shows that, as conversion is increased, the production of light gases plus coke is increased to a greater extent than the gasoline yield.

The effect of temperature on light gases plus coke yield was that, at the higher temperature (FIG. 8), the yields were higher and the yield versus catalyst to oil ratio curve increased more sharply than at 500° C.

The selectivity to gasoline was defined as the ratio of the weight of gasoline to the weight of light gases plus coke in the converted products. FIG. 9 shows a plot of selectivity to gasoline versus catalyst to oil ratio for the twelve experimental conditions. The most significant effect is that of temperature. At a temperature of 550° C., the gasoline selectivity is reduced by about 40% on average as compared to that at 500° C. Selectivity to gasoline was also better at the lower catalyst to oil ratios, although the increase was not so significant.

The assessment of the research octane number (RON) for the gasoline fraction ($C_5$ to $C_{12}$) was performed using the method of Anderson et al, *J. Inst. Pet.*, 1972, 58, pp 83-94, who used a multiple regression analysis to estimate the effective octane numbers for groups of hydrocarbons.

The averaged values of the RON'S for the experimental conditions used are tabulated in Table 2.

TABLE 2

| Research Octane Number (RON) of the Gasoline | |
|---|---|
| Experimental Condition | RON |
| 1 | 94.5 |
| 2 | 94.5 |
| 3 | 96.3 |
| 4 | 95.6 |
| 5 | 96.1 |
| 6 | 96.0 |
| 7 | 98.1 |
| 8 | 98.3 |
| 9 | 97.7 |
| 10 | 97.6 |
| 11 | 97.0 |
| 12 | 96.5 |

RON average for T = 500° C. is 95.5 and
RON average for T = 550° C. is 97.5

The high values obtained indicate the selective capability of the Octacat catalyst to form aromatics, branched hydrocarbons, and olefins.

The effect of catalyst to oil ratio and reaction time on the RON was small. Consistent trends were not observed for the range of conditions used. Using a higher temperature, with catalyst to oil ratio and reactive time held constant, increased the RON. For an increase of 50° C., the RON on average increased 2 numbers from 95.5 to 97.5. This may be explained by slower hydrogen transfer reactions compared to cracking rates at higher temperatures resulting in increased olefin and aromatic content and low paraffin content.

The simulation of fast catalytic cracking (FCC) reactions, as the ones taking place in an industrial riser cracker, were found to be effectively represented in a bench-scale reactor termed the riser simulator.

The paraffinic gas oil cracked using Octacat catalyst showed typical trends in product yields and gasoline research octane numbers as those found in commercial FCC processes. As well, the kinetic parameters obtained from the three-lump model were in the range of literature values, although this comparison must be made under close examination of the catalyst type and feedstock used for each experiment. Also, the riser simulator model accurately describes the cracking transformations without the volumetric flow correction needed in flow reactor models. Subsequently, the molar rate equations may be written in equivalent terms of weight fractions allowing analysis of the kinetic parameters directly from the GC analysis.

The wide range of operating conditions, such as reaction time, temperature and catalyst to oil ratio, possible in the new rise simulator makes it an effective tool for providing diverse kinetic a=data for FCC processes.

Although some fluid-dynamic simplifications are apparent in the unit, a pilot-scale FCC configuration (2-3 m length transfer line) is limited to a narrow range of operating conditions set by the dimensions of the unit. For example, the increase in space time in the tube reactor is limited by the height of the tube, as determined by the choking velocity for the unit. Considering these limitations and the increased complexity and cost involved in a pilot-scale, then a bench mark study, such as one that is conducted in the riser simulator, is fully justified.

Another valuable use of the riser simulator is that which is presently accomplished in industry by MAT test as previously described. This test is effective on a comparative basis where yield patterns of different cracked gas oils can be compared with various catalysts. However, the ability to extrapolate the results of MAT tests to commercial rise units and set with this data appropriate kinetic models is uncertain, due to certain inadequacies of the test (long catalyst times-on-stream and coking profiles in the bed). The riser simulator, on the other hand, has the ability to avoid these uncertainties and at the same time give a quick comparison of hydrocarbon distributions for a given catalyst-feedstock combination under a wide range of operating conditions.

Although preferred embodiments of the invention have been described herein in detail, it will be understood by those skilled in the art that variations may be made thereto without departing from the spirit of the invention or the scope of the appended claims.

I claim:

1. An apparatus comprising a reactor vessel, means for introducing a predetermined quantity of fluid reactant into said reactor vessel, means for withdrawing a reaction mixture including reaction products from said reactor vessel after a predetermined residence time for reactants in said reactor vessel, said reactor vessel comprising means defining a confined reactor volume with an upflow zone and a downflow zone, means in said reactor volume for continuously circulating fluids in said reactor volume upwardly through said upflow zone and downwardly through said downflow zone, means for containing in said upflow zone a predetermined quantity of particulate catalyst, thereby defining said confined reactor volume, said containing means having a screen inlet and a screen outlet, said containing means being of sufficient volume to permit fluidization of said particulate catalyst in said containing means by said fluid flowing upwardly therethrough to form a fluidized bed of catalyst particles, said circulating means being located above said screen outlet to induce a uniform upward flow of fluid through said containing means, said circulating means circulating said fluid about said reactor volume at a rate which provides at any moment during said residence time for such reactants an essentially uniform concentration of reactants through said reactor volume to simulate thereby conditions in a catalytic riser reactor, said circulating means being associated with means to circulate reactant fluid at said rate prior to said reactant introduction means introducing reactant fluid to said reactor.

2. The apparatus of claim 1, wherein said reaction mixture withdrawal means withdraws such reaction mixture form said reactor and transfers such reaction mixture into an environment which essentially immediately ceases further reaction.

3. The apparatus of claim 2, further comprising means for analyzing reaction product composition and means for delivering said withdrawn reaction mixture from said withdrawal means to said means for analyzing reaction product composition.

4. The apparatus of claim 1, wherein said introduction means includes means for passing an inert carrier gas through said reactor prior to introduction of fluid reactant, said circulating means being capable of circulating such inert gas through said bed of catalyst particles to fluidize such particles prior to said introduction means introducing fluid reactants to said reactor, means for stopping said means for passing a carrier gas through said reactor during said residence time of said fluid reactants.

5. An apparatus for testing performance of a catalyst in a gaseous phase catalytic reaction for a given reactant, said apparatus comprising a fluidized bed reactor, said reactor having a vessel and means for heating a wall of the vessel, said reactor further including an inlet and an outlet, means defining an upflow zone and an adjacent downflow zone within said vessel, said means defining said upflow zone comprising an annular baffle with means for supporting said annular baffle centrally of said reactor vessel, said annular baffle defining a hollow vertically extending core with a lower end and an upper opening, an inlet screen being provided at said lower opening and an outlet screen being provided at said upper opening, said hollow core providing sufficient volume for fluidization of a particulate catalyst being tested, at lest one of said inlet screen and outlet screen being removable to permit placement of a catalyst being tested within said hollow core, means located above said upflow zone for circulating fluid upwardly of said upflow zone and downwardly of said downflow zone, said circulating means being a revolving impeller located above said outlet screen, said impeller withdrawing fluid reaction mixture from said upflow zone and redirecting it downwardly in said downflow zone, means for conducting an inert carrier gas to and away from said vessel via said inlet and outlet, means for controlling flow of inert carrier gas through said conducting means, means for injecting a predetermined volume of fluid reactants into said conducting means, said flow control means stopping flow of inert carrier gas once an injected predetermined volume of fluid reactants has entered said reactor vessel, means for withdrawing reaction products from said reactor vessel via said outlet with said flow control means resuming flow of inert carrier gas after a predetermined residence time for such fluid reactants in said reactor vessel, said withdrawal means withdrawing such reaction product into an environment which essentially immediately ceases further reaction, said reactor vessel having a cylindrical reactor chamber, said annular baffle having an outer cylindrical wall spaced form an inner wall of said reactor chamber to define an annular section for said downflow zone, said annular section being of limited volume to provide for rapid recirculation of fluids emerging from said outlet screen back to said inlet screen of a fluidized bed of particulate catalyst to provide at any moment during residence time of fluid reactants in said chamber an essentially constant concentration of reactants in said reactor chamber, and thereby simulate conditions in a catalytic riser reactors, means for rotating said impeller, said impeller circulating said flow of fluid upwardly through said cylindrical-shaped reactor chamber in a uniform manner, and means for mounting a plurality of radially directed baffles in said outer cylindrical wall of said annular baffle to minimize swirling of redirected fluid reaction mixture in said downflow zone.

6. The apparatus of claim 5, further comprising means for vaporizing fluid reactants, said vaporizing means being upstream of said injection means and being fluidly connected thereto.

7. The apparatus of claim 5, further comprising means for heating injected fluid reactants in said conducting means with carrier gas to a predetermined elevated temperature, said control means being operable to stop flow of said carrier gas when injected fluid reactants enter said heating means, said control means being capable of resuming flow of said carrier gas to introduce such heated fluid reactants to said reactor when such heated fluid reactants are at such predetermined temperature.

8. The apparatus of claim 5, wherein said withdrawal means transfers withdrawn reaction mixture including reaction products form said reactor vessel to means for analyzing reaction product composition.

9. The apparatus of claim 5, wherein said injecting means injects a predetermined quantity of oxygen into said conducting means to regenerate during such predetermined residence time a coked catalyst.

* * * * *